(12) United States Patent
Saladin et al.

(10) Patent No.: US 7,016,460 B2
(45) Date of Patent: Mar. 21, 2006

(54) RADIOLOGICAL IMAGING APPARATUS WITH DETECTION OF A COMPRESSION PAD

(75) Inventors: Jean-Pierre Saladin, Bagneux (FR); Emmanuel Roger, Courbevoie (FR); Yann Delmas, Courbevoie (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 204 days.

(21) Appl. No.: 10/668,538

(22) Filed: Sep. 23, 2003

(65) Prior Publication Data

US 2005/0039758 A1 Feb. 24, 2005

(30) Foreign Application Priority Data

Sep. 26, 2002 (FR) ................................... 02 11948

(51) Int. Cl.
*A61B 6/00* (2006.01)
*A61B 6/04* (2006.01)
(52) U.S. Cl. ...................................................... 378/37
(58) Field of Classification Search .................. 378/37, 378/162–166
See application file for complete search history.

(56) References Cited

U.S. PATENT DOCUMENTS

| 4,019,059 | A | * | 4/1977 | Brundin et al. ............. 378/209 |
| 5,386,447 | A | | 1/1995 | Siczek ......................... 378/37 |
| 5,553,111 | A | | 9/1996 | Moore et al. ................. 378/37 |
| 6,459,925 | B1 | * | 10/2002 | Nields et al. ............... 600/427 |
| 2003/0198315 | A1 | * | 10/2003 | Andreasson et al. .......... 378/37 |
| 2004/0064027 | A1 | * | 4/2004 | Zimmerman et al. ....... 600/407 |
| 2005/0063509 | A1 | * | 3/2005 | Defreitas et al. ............. 378/37 |

FOREIGN PATENT DOCUMENTS

DE 10108297 A1 * 9/2002

* cited by examiner

*Primary Examiner*—Craig E. Church
*Assistant Examiner*—Krystyna Suchecki
(74) *Attorney, Agent, or Firm*—Cantor Colburn LLP

(57) ABSTRACT

The detection of a compression pad in a mammography apparatus is automated. A rear face of the pad is provided with identifying and positioning readable by the sensors of a mobile carriage of the mammography apparatus. The reading is converted into a binary word that enables the mammography apparatus to obtain the operating parameters and to automatically associate reading keys with an image. A reading key is, for example, the name of the examination/image associated with the pad.

44 Claims, 2 Drawing Sheets

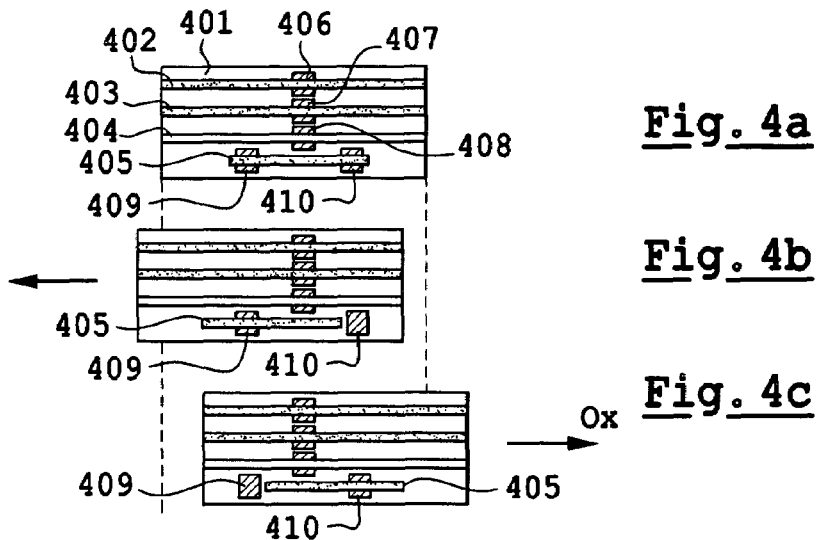
Fig. 4a
Fig. 4b
Fig. 4c
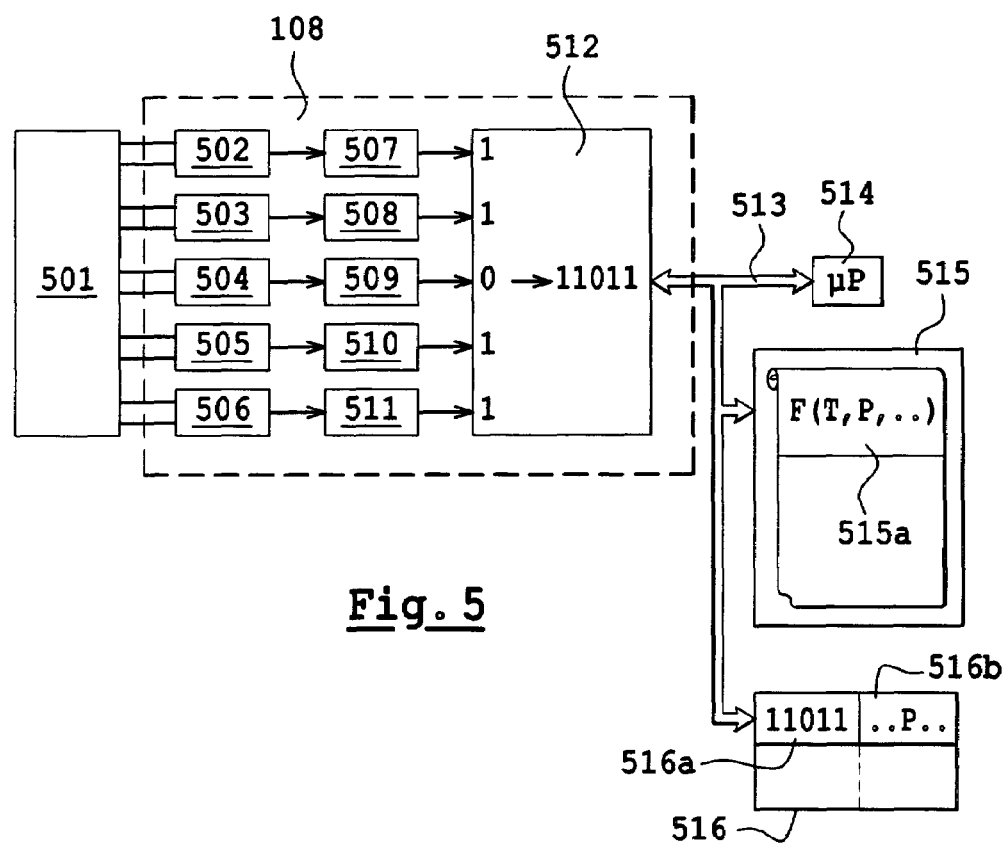
Fig. 5

RADIOLOGICAL IMAGING APPARATUS WITH DETECTION OF A COMPRESSION PAD

CROSS-REFERENCE TO RELATED APPLICATIONS

This application claims the benefit of a priority under 35 USC 119(a)–(d) to French Patent Application No. 0211948 filed Sep. 26, 2002, the entire contents of which are hereby incorporated by reference.

BACKGROUND OF THE INVENTION

The present invention is directed to a radiological apparatus for imaging of an object, and in particular, to a mammography apparatus with detection of compression pad, i.e., a mammography apparatus in which an operator positions the compression pad on its support, and the mammography apparatus will automatically set the parameters for the pad.

A radiological imaging apparatus, such as a mammography apparatus, is an apparatus used to take images of a patient's breast by means of radiation. In practice the apparatus comprises a vertical column bearing a breast-support tray on which the patient breast is placed so that an image can be taken. Beneath the breast-support tray, there is a means for detection, usually a cartridge with a photosensitive film or a digital means, as well as various devices to limit undesirable effects in the image. The top of the column bears means for providing a source of radiation, such as an X-ray tube, whose ray of radiation are directed toward the means for detection.

The acquisition of the mammography image, designed in particular to reveal the presence of microcalcification, which may be evidence of incipient cancer, might be efficient only under certain conditions. One of the conditions is the hardness of the X-rays. The X-rays must be of a hard type so that the image obtained reveals the structures to be detected with sufficient contrast. Furthermore, for reasons of both stability and image quality, the patient's breast has to be compressed. Various compressive forces may be applied. These forces are applied through a compression pad that compresses the breast on the breast-support tray, according to the type of image/examination to be made.

A given type of pad is therefore related to a type of image/examination. Furthermore, a pad is also described at least by its intrinsic properties, namely its shape, dimensions and the absorption characteristics of the material in which it is made. These characteristics of the pad are important because the stream of X-rays travels through the pad before reaching the breast and then the X-ray sensitive receiver/detector making the measurement/image. It is therefore important to be able to take account of these characteristics for the exploitation, or production, of the images resulting from the examination.

In the prior art, the physical characteristics of the compression pad are taken into account either by the operator examining the images or by an algorithm for processing the acquired data and the physician. Whatever the specific situation, the physician must be given reading keys and the algorithm must be provided with processing parameters. These reading keys, or parameters, pertain to the nature of the examination, i.e., they depend on the nature of the view. The views are classified as a function of ranges of angle and position of the image receiver with respect to the breast. Each of these views has a name enabling it to be identified rapidly and simply. For example, there are MLO views (medio-lateral-oblique views of the breast). There also exist Spot views: these are magnified views made with small pads because the observed zone is small. The pads are then called Spot pads. The list of views/examinations is not exhaustive.

In the prior art, the operator at a panel connected to the mammography apparatus enters the parameters, or they are viewed on the image through the interposition, between the detector and the radiation source, of an opaque plate comprising a message used to identify the parameters of the image. Manipulations of this kind entail painful waiting periods for the patient while the breast is compressed. Furthermore, the operator is liable to commit information-recording errors that give rise to confusion during the analysis of the images. Indeed, a key assumes all its significance as a function of these interpretation keys. If these keys are poor, it becomes impossible to interpret the picture and therefore to carry out a diagnosis. At worst, this may lead to a wrong diagnosis. The fact that an operator often has to carry out operations to set the parameter of the apparatus increases the possibility of error through the establishment of routine or of lassitude.

BRIEF DESCRIPTION OF THE INVENTION

An embodiment of the invention is a radiological apparatus, in particular, a mammography apparatus, comprising a column that supports a breast-support tray and a pad for the compression of the breast against the tray, the compression pad being borne by a mobile carriage along the column, wherein the compression pad comprises means for identification of the pad capable of working together with means for reading the mobile carriage, the means for reading working together with a "smart device" of the mammography apparatus for providing an image of a breast, the "smart device" comprising a plurality of tracks and relays.

BRIEF DESCRIPTION OF THE DRAWINGS

The invention and embodiments thereof will be understood more clearly from the following description and from the appended drawings, in which:

FIGS. 4a, 4b and 4c are back views of the compression pad in positions relatives to a mobile carriage and to the reading means of the carriage; and FIG. 5 shows means implemented by the mobile carriage for the reading of the information presented on the compression pad.

DETAILED DESCRIPTION OF THE INVENTION

Figure 1:
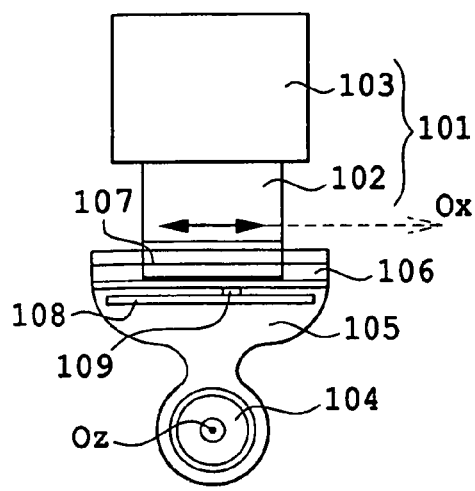
FIG. 1 is a top view of a compression pad and a mobile carriage.

FIG. 1 shows a compression pad 101. In the embodiment, pad 101 has an arm 102 used to move or shift compression block 103 with respect to column 104 of a mammography apparatus (not shown but is well-known in the art). The move or shift is due to constraints related to anatomy and to the space requirement of the mammography apparatus. Pad 101 compresses the breast against a breast-support tray (not shown but is well-known in the art). A breast compressed in this way may then be irradiated optimally, and thus a good image is obtained with minimum radiation.

The compression pad 101 is fixed, through the arm 102, to a mobile carriage 105. Carriage 105 is mobile in translation along an axis Oz. The mobility of the carriage 105 enables a breast to be compressed between the pad 101 and the breast-support tray. The carriage 105 is fixed, through a sliding link, to column 104. The motion of the carriage is obtained either through a worm screw, or through a toothed rack or by any other means or equivalents thereof known to one skilled in the art.

Carriage 105 has a rail 106 in which a bump 107 of the pad is made to slide, the external dimensions of the bump 107 corresponding to the internal dimensions of the rail 106. This enables the mobile carriage 105 and the compression pad 101 to be fixedly joined during motions along the axis Oz of the carriage 105. The introduction of the pad 101 into the carriage 105 is done in a direction Ox perpendicular to the direction Oz. Thus, during compression along the axis Oz, there is no risk that the pad 101 will move along the axis Ox, the compressive force being perpendicular to this axis. However, locking devices, for example, clip-type devices or equivalents thereof, can be used to lock the pad to the carriage once it is in position. Other modes of positioning the pad can be used, for example, modes using hooks.

Carriage 105 also has a printed circuit 108. A surface of the printed circuit 108 is parallel to a rear face of the compression pad 101. The term "rear face" of the compression pad 101 shall be understood to mean that face of the compression pad 101 that is in contact with the mobile carriage 105. The rear face of the compression pad fixed to the mobile carriage 105 is before a front face of carriage 105. The printed circuit 108 comprises at least one reading means 109, for example a relay 109, fixed to circuit 108. Circuit 108 is fixed to the carriage 105 in such a way that the means 109 can read the means of identification of the pad 101. The circuit 108 should preferably be close to the front face of the carriage 105.

Figure 2:
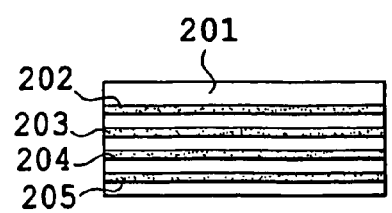
FIG. 2 is a back view of a compression pad.

FIG. 2 shows a rear face 201 of the compression pad. The rear face 201 has parallel tracks, or actuators, 202 to 205. These tracks 202 to 205 are oriented along the axis Ox defined for FIG. 1. The nature of the tracks depends on the nature of the means 109. If the tracks 109 are mechanical relays, then a track is a lengthwise bump of the rear face 201. By its presence, this bump sets up a contact between the two terminals of the relay. A mechanical track of this kind is, for example, a roller track or a slider track of the cam track type, with at least two levels corresponding to two levels of electrical signals. If it is a magnetic relay, the track is then a magnetized track detectable by magnetic relay. If it is an optical relay, the track is then a thin track made of a reflecting substance. Additional equivalent means can be made or proposed by one skilled in the art.

Each track can be seen as an information bit. If the track is present, this means that the bit is at 1. If not, it means that the bit is at 0. The number of relays for the reading of identification information contained in the circuit 108 determines the dynamics of detection by the mammography apparatus. If circuit 108 has three relays for the detection of identification tracks, then the mammography apparatus has a recognition capacity defined by three bits, that is the mammography apparatus is capable of distinguishing $2^3$ rear faces of different compression pads.

In the embodiment of FIG. 2, rear face 201 potentially comprises four tracks. The presence of a track is detected and corresponds to a value 1, the absence of a track corresponds to non-detection and therefore to a value 0.

Thus, with four detectable tracks, namely with four relays for reading position on the circuit 108, it is possible to detect sixteen different states for a rear face, namely sixteen different compression pads. However, for reasons of robustness of the device, it may be preferred to carry out an encoding as follows: three tracks to encode the type of the pad, and one parity track corresponding to the sum of the first three tracks. It is thus possible to detect worn-out tracks or defective relays, and avert errors of parameterization and/or interpretation. It is possible then, for example, to consider the following table, track 1 being the parity track:

| Track 1 | Track 2 | Track 3 | Track 4 | Interpretation: |
|---------|---------|---------|---------|-----------------|
| 0 | 0 | 0 | 0 | No pad |
| 1 | 0 | 0 | 1 | Type 1 pad |
| 1 | 0 | 1 | 0 | Type 2 pad |
| 0 | 0 | 1 | 1 | Type 3 pad |
| 1 | 1 | 0 | 0 | Type 4 pad |
| 0 | 1 | 0 | 1 | Type 5 pad |
| 0 | 1 | 1 | 0 | Type 6 pad |
| 1 | 1 | 1 | 1 | Unrecognized pad |

The identification tracks 202 to 205 extend along the direction Ox so that they can be detected whatever the position of the compression pad on the mobile carriage. This extension is equal to at least two-thirds of the width of the rear face of the compression pad. Tracks 202 to 205 are centered, along the axis Ox, on an axis parallel to the axis Oz and divide the rear face of the pad into two equal parts.

Figure 3:
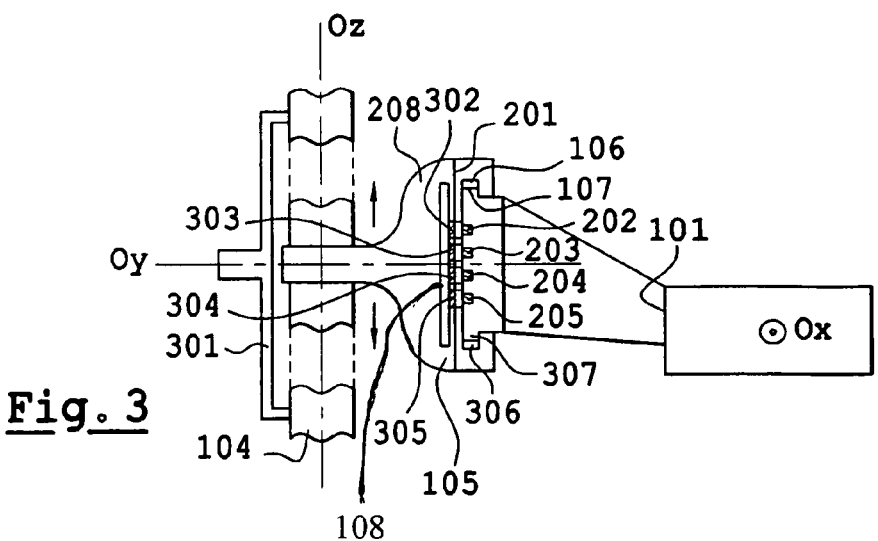
FIG. 3 is a side view of a compression pad and a mobile carriage.

FIG. 3 shows a side view of a device. FIG. 3 shows the mobile carriage on the column 104 along the axis Oz. Column 104 is itself fixed to an arm 301 fixedly joined to the rest of the mammography apparatus (not shown). The arm can pivot about an axis Oy perpendicular to the axes Ox and Oz defined above. The tilt of the arm 301 with respect to a given direction, vertical or horizontal, is accessible to the mammography apparatus. Knowledge of this tilt makes it possible to refine the information obtained by reading of the rear face of the pad during the parameterization of the mammography apparatus or during the production of interpretation keys for an image.

FIG. 3 also shows circuit 108 located in front of the rear face of compression pad 101 fixed to mobile carriage 105. Circuit 108 has four relays 302 to 305 respectively, located so as to be facing tracks 202 to 205, respectively. Tracks 302 to 305 are preferably aligned in parallel to the axis Oz. FIG. 3 show that the carriage 105 has grooves 106 and 306 on the upper part of its front face, and on the lower part of its front face. An upper bump 107 and a lower bump 307 of the pad 101 slide in the grooves. The sliding is done in a direction parallel to the axis Ox. The sliding of the compression pad slide on the mobile carriage makes it possible to position the pad in the appropriate position according to the type of image to be made.

FIGS. 4a, 4b and 4c illustrate the manner for automatically detecting the position of the compression pad on the mobile carriage. A rear face 401 has three tracks 402 to 404 for the identification of the compression pad. The rear face 401 also has a localization track 405 parallel to the identification tracks. To co-operate with the tracks 402 to 404 a carriage has relays 406 to 408 positioned before tracks 402 to 404 once the pad comprising these tracks is positioned on the carriage. The relays 406 to 408, like the relays 302 to 305, are aligned in a direction parallel to the axis Oz. FIGS. 4a, 4b, 4c also illustrate that for one of the identification tracks, in this case the track 404, not to be active. This is means that the track 404 is not present on the rear face of the compression pad, or that the track 404 does not switch over the relay 408.

FIGS. 4a, 4b, 4c show a mobile carriage having several relays associated with a positioning/localizing track. FIGS. 4a, 4b, and 4c show, for example, two relays 409 and 410 that can be actuated by the positioning track 405. Track 405 is an actuator for the relays 409 and 410. A positioning track therefore extends preferably in a direction parallel to axis Ox. The positioning detection relays are placed on the route of track 405 when the compression pad is shifted on the mobile carriage.

Thus, FIG. 4a illustrates a compression pad identified by the active tracks 402 and 403, and by the inactive track 404 is in a central position. This position is determined by two relays 409 and 410 that are activated by the localization tracks 405.

FIG. 4b illustrates a compression pad identified by the active tracks 402 and 403, and by the inactive track 404 that is in a first lateral position. This position is determined by the relay 409 that is activated by the localization track 405, and that the relay 410 is inactive.

FIG. 4c illustrates a compression pad identified by the active tracks 402 and 403, and by the inactive track 404 that is in a second lateral position. This position is determined by the relay 410 that is activated by the localization track 405, and that the relay 409 is inactive.

In another embodiment, there could be a greater number of relays on the route of track 405. This would make it possible to refine the knowledge of the position of the pad on the mobile carriage.

FIG. 5 provides a schematic illustration of the working of circuit 108. FIG. 5 shows a pad 501 that actuates or does not actuate relays 502 to 506. For this explanation, establish a parallel between FIG. 4a and FIG. 5 in making the relays 502 to 506, respectively, correspond to the relays 406 to 410, respectively. For reasons of longevity and reliability, the relays used are preferably of the LVLE (Low Voltage Limited Energy) type in which the operating voltages are incompatible with the operating voltages of the logic circuits. Relays of this kind are, for example, the REED relays. Each relay 502 to 506, respectively, is therefore connected to an input of a level-matching circuit 507 to 511, respectively, that converts the output signals from the relays into signals electrically compatible with control logic. Each output of the matching circuit is furthermore connected to an input of a serializer circuit 512 or parallel-to-serial converter circuit. The serializer circuit 512 also has a connection interface with a bus 513 of the mammography apparatus. Bus 513 is furthermore connected to a microprocessor 514 and to a program memory 515. Memory 515 comprises at least one zone 515a comprising instruction codes by which the microprocessor can interrogate the circuit 512 and thus obtain the state of the relays 502 to 506. The state of the relays 502 to 506 at a date D provides information on the type (relays 502 to 504) of pad fixed to the mobile carriage as well as on the position (relays 505 and 506) of the pad.

In another embodiment, the serializer circuit 512 is replaced by a memory circuit that can be read in parallel. This replacement enables a faster reading of the state of the relays 502 to 506.

At a date D, each relay is in a given state, open 0, or closed 1. A date D therefore has a corresponding state binary word comprising as many bits as there are reading relays on the pad. In an embodiment, the state binary word then makes it possible to address a memory 516. Memory 516 is structured as a table. Each line of the table 516 corresponds to a value of the state word. A first column 516a of the table 516 correspond to a value of the state word, the second column 516b corresponds to parameters associated with this state word. These parameters are parameters corresponding to operations parameterization of the mammography apparatus, parameters for processing measurements made, or parameters used to mark an image so that a practitioner can interpret it.

The position of the pad is interesting in the same way as is the type of pad. A pad does not necessarily have a constant section about its direction of shift with respect to the mobile carriage. A pad therefore does not necessarily absorb X-rays in the same way from one position of the pad to another.

The embodiments of the invention enables the automatic detection of the type of compression pad used for the image, and the position of the pad on the mobile carriage. This information is useful, firstly, for the automatic annotation of the image when it is being acquired, and secondly for the post-acquisition computations made, after the image has been acquired, by a workstation responsible for presenting the image on a means for display such as a screen. This information is also useful for the production of keys for the interpretation of a picture. Such interpretation keys are, for example, the name of the examination, the type of pad used, a tilt value of an arm of a mammography apparatus, etc. These keys are presented in a device, such as a cartridge, of the image presented to the practitioner, and are produced at the same time as the image is produced by the mammography apparatus.

In one pre-acquisition mode, this information can be used to modulate the intensity of the radiation as a function of the quantity of material to be crossed in the pad. This thickness is related both to the type of pad and to its position.

In the description, the printed circuit 108 has been placed directly behind the front face of the mobile carriage 105. In practice, it is possible to use a comb of relays, fixed close to the rear face of the mobile carriage 105 so that the relays of the comb can co-operate with the tracks/actuators of a pad. In this case, the column is connected to the circuit 108 through, for example, a flexible sheet. The circuit 108 can then be positioned anywhere on the mobile carriage 105.

An embodiment of the invention automatically provides the mammography apparatus with information for the exploitation of data acquired during an exposure according to the nature and position of the compression pad.

An embodiment of the invention automatically provides to the mammography apparatus information for establishing the parameters for the irradiation as a function of the nature and position of a compression pad.

The disclosed invention and embodiments thereof provides a compression pad with means for identification. The means for identification work together with means for reading placed on a mobile carriage that supports the compression pad. The means for identification are passive and therefore need no power supply. The means for identification are accessible, in read mode, whatever the position of the compression pad on the mobile carriage. To supplement the information accessible on the pad, it also comprises means for enabling the mobile carriage to read the position of the pad in relation to the carriage. Knowledge of this position makes it possible to take account of the specific characteristics of shape of the pad during irradiation.

The means for reading are, for example one or more relays, which may be mechanical, optical or magnetic. The means for identification and means for positioning are tracks extending in a direction along which the pad is mobile so that it can be positioned for example, with respect to the mobile carriage. Through this extension of the means for reading, the identification of the pad can be made independent of this position with respect to the carriage.

One skilled in the art may make or propose various modifications to the structure and/or manner and/or way and/or function and/or means and\or result and equivalents thereof to the disclosed embodiments without departing from the scope and extent of the invention.

What is claimed is:

1. A radiological imaging apparatus having a means for supporting an object tray and an object thereon, the apparatus comprising:
   means for compression of the object against the tray;
   the means for compression carried by a mobile carriage along the means for support, the means for compression having a direction of mobility relative to the mobile carriage that is other than a direction of compression of the object;
   the means for compression comprising means for the identification of the means for compression cooperating with means for reading of the mobile carriage irregardless of a lateral displacement of the means for compression relative to the means for reading;
   the means for reading cooperating with a smart device of the apparatus for providing an image of the object.

2. The apparatus according to claim 1 wherein the means for identification of the means for compression comprise a relay actuator.

3. The apparatus according to claim 2 wherein the means for reading of the mobile carriage comprise a relay that can be actuated by the means for compression.

4. The apparatus according to claim 3 wherein the means for reading comprises, in series, a circuit for adapting voltage to levels compatible with a logic circuit and a parallel-to serial converter circuit.

5. The apparatus according to claim 3 wherein the means for identification of the compression pad extends along a direction of mobility of the pad with respect to the mobile carriage.

6. The apparatus according to claim 3 wherein the mobile carriage comprises means for reading the position of the compression pad, the compression pad comprising means to indicate its positioning.

7. The apparatus according to claim 2 wherein the relay is mechanical, magnetic, and optical, or any combination comprising at least one of the foregoing relays.

8. The apparatus according to claim 7 wherein the means for reading comprises, in series, a circuit for adapting voltage to levels compatible with a logic circuit and a parallel-to serial converter circuit.

9. The apparatus according to claim 7 wherein the means for identification of the compression pad extends along a direction of mobility of the pad with respect to the mobile carriage.

10. The apparatus according to claim 7 wherein the mobile carriage comprises means for reading the position of the compression pad, the compression pad comprising means to indicate its positioning.

11. The apparatus according to claim 7 wherein the mobile carriage comprises means for reading the position of the compression pad, the compression pad comprising means to indicate its positioning.

12. The apparatus according to claim 2 wherein the means for reading comprises, in series, a circuit for adapting voltage to levels compatible with a logic circuit and a parallel-to serial converter circuit.

13. The apparatus according to claim 2 wherein the means for identification of the compression pad extends along a direction of mobility of the pad with respect to the mobile carriage.

14. The apparatus according to claim 2 wherein the mobile carriage comprises means for reading the position of the compression pad, the compression pad comprising means to indicate its positioning.

15. The apparatus according to claim 1 wherein the means for reading of the mobile carriage comprise a relay that can be actuated by the means for compression.

16. The apparatus according to claim 15 wherein the relay is mechanical, magnetic, optical, or any combination comprising at least one of the foregoing relays.

17. The apparatus according to claim 15 wherein the means for reading comprises, in series, a circuit for adapting voltage to levels compatible with a logic circuit and a parallel-to serial converter circuit.

18. The apparatus according to claim 15 wherein the means for identification of the compression pad extends along a direction of mobility of the pad with respect to the mobile carriage.

19. The apparatus according to claim 15 wherein the mobile carriage comprises means for reading the position of the compression pad, the compression pad comprising means to indicate its positioning.

20. The apparatus according to claim 16 wherein the means for identification of the compression pad extends along a direction of mobility of the pad with respect to the mobile carriage.

21. The apparatus according to claim 1 wherein the means for reading comprises, in series, a circuit for adapting voltage to levels compatible with a logic circuit and a parallel-to serial converter circuit.

22. The machine according to claim 21 wherein each output of a matching circuit is connected to an input of the parallel-to-serial converter circuit.

23. The apparatus according to claim 22 wherein an input of a matching circuit is connected to the output of a relay.

24. The apparatus according to claim 22 wherein the means for identification of the compression pad extends along a direction of mobility of the pad with respect to the mobile carriage.

25. The apparatus according to claim 22 wherein the mobile carriage comprises means for reading the position of the compression pad, the compression pad comprising means to indicate its positioning.

26. The apparatus according to claim 21 wherein an input of a matching circuit is connected to the output of a relay.

27. The apparatus according to claim 26 wherein the means for identification of the compression pad extends along a direction of mobility of the pad with respect to the mobile carriage.

28. The apparatus according to claim 26 wherein the mobile carriage comprises means for reading the position of the compression pad, the compression pad comprising means to indicate its positioning.

29. The apparatus according to claim 21 wherein the means for identification of the compression pad extends along a direction of mobility of the pad with respect to the mobile carriage.

30. The apparatus according to claim 21 wherein the mobile carriage comprises means for reading the position of the compression pad, the compression pad comprising means to indicate its positioning.

31. The apparatus according to claim 1 wherein the means for identification of the compression pad extends along a direction of mobility of the pad with respect to the mobile carriage.

32. The apparatus according to claim 31 wherein the mobile carriage comprises means for reading the position of the compression pad, the compression pad comprising means to indicate its positioning.

33. The apparatus according to claim 32 wherein the means for reading the position comprise a series of at least two position-detector relays aligned in a direction of shift of the compression pad with respect to the mobile carriage.

34. The apparatus according to claim 33 wherein the compression pad comprises relay actuators working together with the position-detector relays during and after the placing of the compression pad on the mobile carnage.

35. The apparatus according to claim 33 wherein the means for indicating the positioning of the compression pad extend along a direction of mobility with respect to the mobile carriage.

36. The apparatus according to claim 34 wherein the means for indicating the positioning of the compression pad extend along a direction of mobility with respect to the mobile carriage.

37. The apparatus according to claim 1 wherein the mobile carriage comprises means for reading the position of the compression pad, the compression pad comprising means to indicate its positioning.

38. The apparatus according to claim 37 wherein the means for indicating the positioning of the compression pad extend along a direction of mobility with respect to the mobile carnage.

39. The apparatus according to claim 1 wherein the control device comprises a plurality of tracks affixed to the pad, each track providing means for identifying the position of the pad.

40. The apparatus of claim 39 wherein the control device comprises a plurality of relays.

41. The apparatus according to claim 39 wherein the control device comprises means for digitally identifying the position of the pad.

42. The apparatus according to claim 40 wherein the control device further comprises a processor responsive to coded instructions for determining the state of the relays.

43. A radiological imaging apparatus having a column for supporting an object tray and an object thereon, the apparatus comprising:

a source of x-rays; an x-ray imaging device;

a compression pad for compressing the object against the tray;

a mobile carriage for carrying the compression pad in a first direction along the column, the compression pad movable laterally in a second direction perpendicular to the first direction;

a plurality of identification tracks disposed at the compression pad and extending along the second direction, the identification tracks for identifying the compression pad;

a track reader disposed at the mobile carriage and cooperating with the identification tracks irregardless of a lateral displacement of the compression pad in the second direction relative to the track reader and a processor controlled device cooperative with the track reader for providing information for imaging of the object.

44. The apparatus according to claim 43, wherein:

the processor controlled device is configured to automatically identify the type of compression pad and the position of the compression pad relative to a lateral displacement of the compression pad in the second direction.

* * * * *

UNITED STATES PATENT AND TRADEMARK OFFICE
CERTIFICATE OF CORRECTION

PATENT NO.       : 7,016,460 B2                                              Page 1 of 1
APPLICATION NO.  : 10/668538
DATED            : March 21, 2006
INVENTOR(S)      : Saladin et al.

It is certified that error appears in the above-identified patent and that said Letters Patent is hereby corrected as shown below:

Column 2:
Line 34, after "a" delete "smart" and insert therefor -- control --
Line 35, after "the" delete "smart" and insert therefor --control--

Column 7:
Line 11, after "thereon," insert -- means for providing a source of x-rays; means for providing an x-ray image;--
Line 46, after "magnetic," delete "and"

Column 8:
Line 36, after "The" delete "machine" in claim 22 and insert therefor -- apparatus --

Column 10:
Line 26, after "reader" insert -- ; --

Signed and Sealed this

Nineteenth Day of September, 2006

JON W. DUDAS
*Director of the United States Patent and Trademark Office*